United States Patent [19]

Guédon born Saglier et al.

[11] Patent Number: 4,533,635

[45] Date of Patent: Aug. 6, 1985

[54] PROCESS FOR STIMULATING THE GROWTH OF EPIDERMAL CELLS

[75] Inventors: Isabelle Guédon born Saglier; Denis Barritault, both of Paris; Yves Courtois, Gif sur Yvette; Cristina Arruti; Michel Prunieras, both of Paris, all of France

[73] Assignee: Institut National de la Sante et de la Recherche Medicale, Paris, France

[21] Appl. No.: 237,153

[22] PCT Filed: Jul. 10, 1980

[86] PCT No.: PCT/FR80/00118

§ 371 Date: Feb. 18, 1981

§ 102(e) Date: Feb. 18, 1981

[87] PCT Pub. No.: WO81/00260

PCT Pub. Date: Feb. 5, 1981

[30] Foreign Application Priority Data

Jul. 13, 1979 [FR] France ............... 79 18282

[51] Int. Cl.$^3$ .............................................. C12N 5/00
[52] U.S. Cl. ........................................ 435/240; 435/1; 435/241; 128/334 R
[58] Field of Search ................... 424/95; 435/240, 241, 435/1; 128/334 R

[56] References Cited

U.S. PATENT DOCUMENTS 4,299,819 11/1981 Eisinger ............................... 435/241

OTHER PUBLICATIONS

Barritault et al.—Chem. Abst., vol. 92, (1980), p. 178272c.
Barritault et al.—Ophthalmic Res., vol. 11, (1979), pp. 316–321.
Gospodarowicz et al.—Nat. Canc. Inst. Mono 48, (1978), pp. 109–130.
Barritault et al.—Differentiation, vol. 18, (1981), pp. 29–42.
Gospodarowicz—Nature, vol. 249, (1974), pp. 123–127.
Green—Cell, vol. 15, (1978), pp. 801–811.
Gospodarowicz et al.—Exp. Eye Res., vol. 25, (1977), p. 631.
Arruti et al., Experimental Cell Research, vol. 117, No. 2, pp. 283–292, (1978).
Rheinwald et al., Nature, vol. 265, No. 5593, pp. 421–424, (1977).
Kasavina et al., Chemical Abstracts, vol. 55, No. 5, Abstract 4892c, (1960).
Karasek, Chemical Abstracts, vol. 77, No. 11, Abstract 73097m, (1972).

*Primary Examiner*—Sam Rosen
*Attorney, Agent, or Firm*—Oblon, Fisher, Spivak, McClelland & Maier

[57] ABSTRACT

A process for stimulating the growth of human epidermal cells, applications of said process and products applying the said process.

A process for stimulating the growth of epidermis cells.

The epidermis cells are contacted with an aqueous saline extract (RE) of ocular tissues. The process is especially applied for human epidermis cells.

Application to the study of chromosomes of the human epidermis cell, particularly for the detection of natural or induced chromosome anomalies, and to the production of grafts, and especially autografts, usable on man, for example in the treatment of burns, cosmetic and diagnostic products.

14 Claims, No Drawings

PROCESS FOR STIMULATING THE GROWTH OF EPIDERMAL CELLS

This invention relates to processes and products applicable to the human skin and more particularly to the adult human epidermis. Its object is notably a process for stimulating the growth of human epidermal cells, particularly those of adults, as well as cosmetic, pharmaceutical and diagnostic products using the said process.

The skin is the principal tissue exposed to the mutagenic effects of chemical and physical environmental agents. This is particularly true of radiations of every sort. The skin is composed of tissues of mesenchymal origin (the derma and the blood vessels) and tissues of ectodermic origin (the epidermis). Now, although it is known to extract mesenchymal cells (fibroblasts) from the dermis to culture them and to study the mutagenic and carcinogenic effects of chemical and physical environmental factors, it is difficult to extract them from the epidermis. One of these difficulties had not yet been overcome. This is the application of processes of cytogenetic examination to cultured adult epidermal cells, which involves on the one hand the preparation and analysis of chromosomes, and on the other, the notation of sister chromatid exchanges (SCE). In point of fact, although a few rare publications mention succinct chromosomic investigations, there is no exhaustive chromosomic investigation, particularly in so far as heriditary human skin diseases are concerned and, to the best of the applicant's knowledge, no bibliographical references exist with respect to SCE.

A series of recent investigations suggests that the increase of SCEs is a sensitive and accurate indication of the mutagenic effect of a chemical product or of a radiation. The application of SCE-revealing techniques to adult human epidermal cells is, therefore, unquestionably important.

The object of the invention is, notably, a process applicable to the preparation and the analysis of chromosomes and to the preparation and the notation of SCEs. According to the invention, it is possible to induce mitotic multiplication of these cells on a normally hostile glass substrate.

The invention also makes it possible to provide a solution to all the problems connected with the growth and culture of epidermal cells, particularly in man and especially in adults. Thus, apart from the abovementioned cytogenetic application, the invention can also be used in the treatment of burns, in the fields of cosmetics and of cutaneous pharmacology and for long-term culture of epidermal cells.

The present invention calls upon previous work reported by ARRUTI C. and COURTOIS Y. Exptl. Cell. Res. 117, 283-292 (1978). These authors established that a retinal extract, referred to by the abbreviation RE, was a growth-promoting factor for cultured epithelial lens cells. The skilled artisan can, if needs be, refer to this article to obtain the necessary information on this retinal extract RE, and the properties which have been observed. The authors used a total retinal extract obtained by extraction with an aqueous salt solution, with a pH 7.2 phosphate buffer such as the type sold by FLOW Laboratories Ltd. The bovine retinas are placed in intimate contact with such a solution. After a certain number of physical centrifugation and filtration techniques the retinal extract RE is isolated. However, the observations reported in this article are limited to the growth of epithelial lens cells.

Certain documents relating to the prior technique describe work on extracts obtained from animal ocular tissue.

French Pat. No. 71.13.756 (publication 2.134.088) describes a process for obtaining a total bovine eyeball extract. The series of steps involves the action of merthiolate, of an alcaloid and of "Celite".

The alcoholic extract so obtained is applied in the field of ophthalmology. It is not, therefore, an aqueous saline solution, and its use for the growth of epidermal cells is not mentioned.

The article by B. S. Kasavina et al. (Columbus, Ohio, USA) and SU Pat. No. 130.159 of the July 15, 1960 cited in Chemical Abstracts Vol. 55, No. 5 (Mar. 6, 1961) No. 4892c describe the preparation of a product containing hyaluronic acid by extraction from the vitreous humour of cattle eyes, and its application to the treatment of infected wounds. The product is a chloroformic extract.

The article by M. A. Karasek in J. Invest. Dermatol. 1972, 59 (1), 99-101, cited in Chemical Abstracts Vol. 77, No. 11 (Sept. 11, 1972) No. 73 097 m, p. 305, deals with the in vitro growth of epidermal cells in the presence of a certain number of factors. It is established that hyaluronic acid did not stimulate epithelial cells. This article also shows that it is impossible to forsee the effect of a determined factor on epidermal cell growth.

It is therefore clear that the prior technique does not teach a factor consisting of an aqueous extract of ocular tissue that is effective in stimulating the growth of epidermal cells, particularly adult, especially human, epidermal cells.

According to the present invention, the growth of cultured epidermal cells can be stimulated irrespective of the age and the species of the donor, by using the growth factor RE. Also according to the invention, the growth factor RE is effective on adult, and particularly on human epidermal cells.

In its most general form, the invention relates to a process for stimulating the growth of epidermal cells particularly adult cells, with an aqueous salt extract of ocular tissue, i.e. eyeball tissue, (or RE extract).

To obtain the active RE agent, the technique described in the abovementioned article by C. Arruti and Y. Courtois can be used. The starting material, namely bovine retinas, is easily available and abundant.

The expression "ocular tissue extract" designates a product that can be extracted from various tissues of the eye, such as the choroid, the iris and the vitreous humour. This definition does not include the crystalline lends and the aqueous humour, tissues that do not contain RE.

To effect extraction, any aqueous salt solution is used, buffered to a pH of approximately 7.2 and capable of providing an aqueous extract containing the RE.

Surprisingly, it was ascertained that by using the RE factor, according to the invention, in adult human epidermal cell cultures, it became possible to provide a solution to problems that had not been solved by the prior technique. For example, the invention makes it possible to effect chromosome analysis and the evaluation of SCEs in in vitro cultures of adult human keratinocytes, through the activation of the mitotic activity of keratinocytes resulting from the use of RE.

The activator effect of RE on the growth of epidermal cells will be illustrated below. An increase in the surface covered in a given number of days by the same number of seeded cells is observed. The cell density per unit area revealed by staining is greater for the treated cells. This stronger staining is not due to an increase in the height of the cells but to an increase of mitotic activity.

As has already been stated hereinabove, it was impossible to prepare metaphasic chromosomes of adult human cells in the absence of cellular growth activities; see, for example, Green H. Cell. 15, 801-811 (1978). Cells on glass slides in an ordinary culture medium (TCM) in the presence of RE makes it possible to obtain a number of mitoses necessary for the requirements of the invention. According to the facts established in the prior art, the primary keratinocyte cells tend to pile up and to keratinize. Thus, somme metaphases are situated under one or more layers of cells, which prevents chromosome dispersion. Part of the "spontaneous" mitoses is therefore lost and too few remain. On the other hand, the addition of RE induces a marked increase in mitotic activity which, in combination with a 15 hour treatment with colchicine salt, available under the trade name of "Colcemid" (Gibco), makes it possible to prepare a sufficient number of well spread out metaphases. An average of 20 analysable metaphases per slide can be obtained in routine operation.

The effect of RE on adult epidermal cells differs from the effect of the product EGF (Epidermal Growth Factor), see COHEN S. and ELLIOTT G. A. J. I, vest. Dermatol., 40, 1-5 (1963), and COHEN S. in Hormones and Development, Hamburgh M. and Burrington E. J, ed. Meredith Corp. N.Y., 753-766 (1971), which is essentially active on foetal cells or cells from newborn infants. Furthermore, these two mitogenic agents differ completely by their action on other target cells.

It has also been established that RE was not mutagenic, which is a very important characteristic for adult epidermal cells. This property can, moreover, be used for the detection of the action of mutagens. Experiments have shown that the increased growth of the cell culture, was indeed due to an actual multiplication of keratinocytes, and not to that of possible fibroblasts which might have been detached from the dermis during trypsinization. For example, phase contrast microscope examination reveals that the cultures are composed of a single cell type, having the appearance of an epithelium. Furthermore, the reaction to the leucine-aminopeptidase (LAP)enzyme marker of cells of mesenchymal origin in vivo (NACHLAS N. M., CRAWFORD D. T. and SELIGMAN A. M. J. Histochem. Cytochem. 1957, 5, p. 264-278) and in vitro (FRITSCH P., DIEM E. Arch. Derm. Forsch 243, 364-372 (1972), REGNIER M., DELESCLUSE C. and PRUNIERAS M., Acta Dermatovener, 53, 241-247 (1973)) was used to detect dermic fibroblasts, and was completely negative.

The RE growth potentialization effect on adult human epidermal cells may be put to many applications.

In one application, given as an example, the invention makes it possible to effect chromosomic analysis and assessment of SCEs in in vitro cultures of adult human keratinocytes. Well dispersed metaphasic chromosomes can be prepared in a number sufficient for karyotypic analysis and also SCEs can be counted in this cell type.

Cytogenic methods, and particularly the techiques for assessing sister chromatid exchanges (SCE), have recently been developed (see PERRY P. and Wolff S. Nature 251, 156-158 (1974)). This last technique is of special interest in cutaneous pharmacology as the number of exchanges is directly connected with mutagenesis (PERRY P. and EVANS H. J., Nature 258 121-125 (1975) and CARRANO A. V., THOMPSOM L. H., LINDL P. A. and MINKLER J. L., Nature 271, 551-553 (1978). For this reason SCE counting is invaluable for estimating the carcinogenic potential of a cosmetic product, or a therapy or, more generally, of a voluntary or accidental exposure to chemical or physical enviromental factors (all forms of radiations). In the literature, there is very little information on the cytogenetics of epidermal cells and there is no work reported on SCEs. This dearth of information is doubtless due to three major difficulties.

The first lies in the spreading of chromosomes. Trypsin is usually used to harvest cells in mitosis and to disperse chromosomes. However, to harvest adult cultured keratinocytes, EDTA must be used in addition to trypsin (RHEINWALD, J. G. and GREEN H., Cell., 6, 331-344 (1975)) and EDTA interfers with cell swelling in hypotonic solution, which is a fundamental requisite for good chromosome spreading. The chromosomes can be dispersed satisfactorily by directly treating the culture in situ, but the experimentor then comes up against a second difficulty, because glass is the best surface for chromosome spreading, but it is a bad substrate for attaching keratinocytes (LIU S. C. and KARASEK M. J. Invest. Dermatol. 71, 157-162 (1978)).

The third difficulty is that, to obtain SCE, two cycles of consecutive replication of the same cells are necessary to visualize the differential labelling of chromatids with the technique of substitution with bromo deoxyuridine (BUdR) (WOLFF S. and PERRY P. Chromosome 48, 341-353 (1974)—KATO H. nature 251, 70-72 (1974)). The culture must therefore possess a high level of mitotic activity, which is not the case of adult human keratinocyte cultures on a glass substrate.

For the preparation of SCEs it is most important that an appreciable number of cells should divide synchronically. As was said hereinabove, two cell cycles are necessary for a same cell to have one of its DNA strands bisubstituted with BUdR, an indispensable preliminary to visualization of SCEs. Furthermore, both these cycles must for practical reasons, take place in a reasonable period of time (50-70 hours).

The epidermal cells in primary culture are not synchronized and the cells that replicate at a given moment do not necessarily belong to the same group of replicating cells. This means that only a portion of the replicating cells might undergo a second replication cycle during the relatively short period of time available. The great advantage of RE is that it induces sufficient synchronization to enable about 50% of the metaphases to be bisubstituted in about 60 hours. The SCEs can then be counted on about 10 metaphases per slide.

According to one embodiment, a preliminary normal culture of epidermal cells is effected without the growth factor. In a period of between 5 and 10 days, for example at the end of 8 days, a first effective amount of RE is introduced. The following day, or 48 hours later, a further application of RE is made to obtain a second cell replication.

However, this embodiment is only given by way of example. As a variant, the RE can be introduced at the beginning of the operation, but care must be taken to see that cell development is synchronized. If this variant of the procedure is adopted, the RE must be introduced into the cell culture at the start and the culture then arrested to enable synchronization of the cells.

The invention therefore relates to diagnostic products, making it possible to study adult human epidermis cell chromosomes. Such products and the processes for embodying them can make it possible to detect natural or induced chromosome anomalies. Inductive factors are, notably, irradiations as, for example, those resulting from the action of UV rays, or from accidental phenomena, as well as all radiations, such as gamma rays, X rays, neutrons, etc. Among the disorders that can be detected the following may be mentioned: genetic disorders, psoriasis and all types of skin cancers. The adult keratinocyte cells are recognized as target cells for skin carcinogenesis. The advantage of the invention is that it permits direct study of human epidermal cell behaviour, and that it does not require in vivo experimentation, as was the case in the known technique, on partial cell samples, such as fibroblasts.

The invention can be applied, as a preventive measure to study the behavior of skins in certain environments, for example to choose the personnel to work in a nuclear environment.

In such applications, the invention makes use of the fact that RE does not induce mutagenesis. For example, when chromatid exchanges are counted, the exchange rate is observed to be lower that 3 per mitosis, which corresponds to a very low figure that is usually called "spontaneous chromatid exchanges".

It has also been established that the RE used according to the invention is not toxic. When the dose of RE is doubled the cells do not die. This property is obviously very important for the applications which will now be described.

From another point of view, the invention is applicable to a process for making grafts. It is known that, for the treatment of burns, it is important to be able to use the remaining intact skin in order to avoid the problems arising from the immune defenses of the receiver in the case of heterologousgrafts. It is therefore preferable to take pieces of skin from the burn victims themselves to effect autografts. The tissue removed is then separated mechanically in order to multiply by two or three the area covered as the result of the growth of the excised skin. An important improvement has been made to this technique (see IGEL H. J., FREEMAN A. E., BOECKMANN C. R. and KLEIFLED K. L. Arch. Surgery 1974, 108, 724–729).

According to the technique proposed by these authors, pieces of skin are excised in the form of small fragments for subsequent autografting. The fragments are split 3 to 5 weeks prior to grafting, and it is therefore advisable to cultivate this skin. The major problem lies in the transport of epidermal cells. The skin fragments are placed on flags of slaughtered pig skin. Some three weeks later the pig skin is covered with an epidermis culture. This is an advantageous technique as it enables pieces of skin to be taken from the patient's own body. Furthermore, there are no undesirable reactions to the pig skin. An area of 20 to 40 times the area of the original fragments is thus obtained.

There are, however, certain drawbacks to this technique. The portion of the graft placed on the patient's tissue is in contact with the latter through the dead epidermis of the pig skin carrying the cultured epidermis. The presence of the pig skin constitutes an undesirable foreign body. Another drawback lies in the mechanical splitting of the skin used as the graft, as the fragments are necessarily fairly large. It is desirable to obtain ultimate splitting, which, in an ideal case, consists of a single cell. An even more advantageous technique has been proposed recently, derived from the above-mentioned IGEL and FREEMAN technique, and in which the graft is split by an enzymatic process 1 to 2 weeks before being grafted. This period is used to effect in vitro proliferation of the epidermal cells. In order to provide these cultured epidermal cells with a substrate permitting them to proliferate in vitro, and then to be transplanted, the epidermis was removed from thin flaps of human or pig skin. The flaps of derm so obtained were killed and conserved by freezing. The advantage of flaps of dermis with the epidermis removed is that they carry their "lamina densa", in other words a layer of collagen on which the epidermal cells fasten and proliferate. Recombined grafts are thus obtained formed of allo or xenogenic derm covered with autologous epidermis. Grafts of this sort make it possible to multiply the area epidermized by about 80 in two weeks. A technique of this sort was described, for example, in a report made at the 4th national meeting on care for burn victims. May, 21–22, 1979 at La Baule, France.

Whatever the grafting technique used, it is essential to increase the speed of proliferation of the epidermal cells. The advantage of obtaining extensive cultures and, even more important, of being able to effect the culture in a relatively short time, in, for example, a week or less, in order to treat the patient effectively, is indeed obvious.

The invention can advantageously be applied to such a cell culture, as the area covered by the growth of epidermal cells will be proportional to the activity of the growth factor RE. The use of RE provides advantages because, as was mentioned hereinabove, it does not induce mutagenic reactions. It is also established that epidermal cells are modified after their growth in the presence of RE. The process of the invention is, therefore, advantageously applied in the production of grafts for use in the treatment of burns.

By removing a small piece of skin, for example approximately 2 to 3 cm$^2$, a suspension of epidermal cells can be obtained. As was previously stated, culture can be initiated and the cell colonies grow sufficiently in about 8 days. The addition of retinian extract RE for 2 consecutive days makes it possible to obtain mitosis synchronization.

From still another point of view, the invention has to do with cosmetic applications. Conventional cosmetic agents have an effect on the part of the body to be treated, for example, the skin or the hair. However, it is established that cosmetic formulae have an increasing tendancy to contain agents that effect metabolism. Insofar as concerns application to the skin, for example, products that increase epidermal cell growth are sought, as it has been established that the said growth improves the satiny appearance of the skin. Similarily, manufacturers are engaged in preparing products that encourage hair growth when they are applied to the hair or the scalp.

According to the invention, RE can be introduced directly into a presentation suited to cosmetic applications. The presentation must, of course, be adapted to the cosmetic application sought, whether it be, for example, skin regeneration, the fight against signs of ageing or an application to the hair. Furthermore, RE can be used in more specific applications, particularly for the treatment of deficient epidermal cells.

Most of the active agents known in this field cannot be used for the direct treatment of the skin. Many of them are obtained from euphorbia and are considered to be cocarcinogenic. Generalized application should therefore be avoided. The epidermal growth factor E.G.F. appears to be inactive in vivo, or at least, no in vivo activity has been demonstrated. In addition, it is expensive to produce. Therefore cosmetic applications of such a product on a large scale are not likely. The property of chlolera toxin to activate the skin vigorously is known, but such a product is difficult to manipulate.

According to the invention, on the contrary, RE can be used for its activity on the cells of the epidermis, taking advantage of the fact that it is not toxic.

Thus, the invention relates to a cosmetic composition characterized in that it comprises, as active agent, RE. Such a composition can be applied locally to the part of the body to be treated.

For the requirements of the invention, any of the vehicles already proposed for application to the skin or the hair can be used, notably compositions in the form of lotions, gels, creams, ointments, etc. Examples of compositions suited to local application are described by B. KAMMERAU et al. in Arch. Derm. Res. 255 31–42 (1976).

The amount of RE to be used in the compositions of the invention depends on the application considered. Of course, local application can be repeated to provide the necessary amount of active agent. Generally speaking rates of 50 to 400 $\mu$g of total proteins of RE per ml of epidermal cell culture have been found to be satisfactory. Rates in the range of 50 to 100 $\mu$g are preferred.

The invention is also applicable to a long term epidermal cell culture process.

Studies on adult human skin cells meet with many difficulties, especially when adult human epidermis cells are concerned. This is the reason why most experiments are conducted on non-epidermal cells, especially fibroblasts. Fibroblasts are known to possess growth properties in culture that enable practical experiments to be conducted. However, growth of fibroblasts in culture is limited, especially in the case of human cells. A sort of programming exists for human fibroblasts that prevents them from doubling indefinitely. Then again, it is known that the number of fibroblast doublings is greater with embryonic cells then with adult cells. In the case of adults, the culture dies after some thirty doublings. Some animal cells, for example, mouse cells, appear to escape this rule, but, in the case of man, the only means of altering this natural growth limitation control is to introduce viruses or other exogenic substances into the cell culture.

The growth limitation already observed in connection with fibroblasts is still more marked with epidermal cells. Cultures of newborn epidermis cells can be doubled 4 or 5 times, whereas cells from adult skin undergo practically no doubling.

The best system known at present for prolonging long-term cultures of human epiderm was proposed in RHEINWALD and GREEN'S article mentioned above. It consists in coculturing human epidermal cells with irradiated 3 T 3 mouse fibroblasts as the nutritions substrate. These irradiated cells have the property of enhancing the binding of human keratinocytes during culture doubling, and of providing them with nutritions substances of conjunctive origin that increase their growth. The irradiation blocks their own multiplication.

Moreover the 3 T 3 mouse cells have a somewhat inhibiting effect on the growth of human fibroblasts, thus enabling the authors to control the purity of their cultures while starting with what may sometimes be very heterogenous suspensions. During the various culture doubling steps any possible human fibroblasts are removed by the action of the EDTA, at the same time, as the 3T3 mouse cells; the human keratinocytes remaining attached to the substrate, subsequently to be detached by mechanical and enzymatic means. The long-term culture system can have added to it various growth factors, that is to say, products capable of stimulating cell growth, and particularly that of cells extracted from adult tissues. In this connection, COHEN S., and ELLIOTT G. A. in J. Invest. Dermatol. 40 1–5 (1963) described a product capable of enhancing the growth of mouse epidermis cells. Culture experiments were conducted and the authors (RHEINWALD J. C. and GREEN H. Nature 1977,265,421–424) found that this growth factor is effective on newborn epidermal cell cultures.

The question of the activating effect of EGF on the growth of adult epidermal cells remains to be solved. In culture, and in the presence of 3T3 mouse cells, a certain activity on human cells, was reported. Used alone on guinea pig cells, it proved to be ineffective. Finally, on the whole subject, proof of activation is lacking.

Other activators have been described and, as a bibliographical reference, mention may be made of the article by D. GOSPODAROWICZ in Nature 249 (1974) 123.

The author describes a growth factor designated by the abbreviation F.G.F, but no indication can be found of this product activity in the growth of human epidermal cells.

Choleraic toxin has also been studied in human keratinocyte cultures (GREEN H. Cell 1978, 15 801–811). Contrary to its action on many other of the cells studied, this product strongly activates the growth of human keratinocytes, particularly those of newborn humans. However, it is bound firmly to cell membranes, and this bond is non-reversible.

According to the invention, cells can be directly cultured on a substrate, such as a plastic substrate, without the addition of other cells. The RE acts as the nutritive factor, its rather negative action on fibroblasts making it possible for a culture, that has previously been purified, that the amount of possibly contaminating fibroblasts be stabilized at a very small number. The life span of the culture in thus increased in a very simple way. Furthermore, the unquestionable effect of RE on adult cells makes it a valuable mitogenic agent for the material which only reacts weakly to the previously described culture system with 3 T 3 mouse cells. The cytogenetic studies described above further show that this product has no effect either on chromosomes or on the exchanges of keratinocyte chromatids. It is not, therefore, a priori, suspected of having toxic or carcinogenic effects on these cells.

By the use of RE according to the invention, adult human keratinocyte cultures can thus be prolonged. Such a culture process is very easy to implement. It further respects the normal nature of adult human keratinocytes, only providing them with a mitogen nutritive supply of physiological animal origin.

The invention will now be illustrated in greater detail, while in no way being limited thereto, by experiments on adult human epidermal cell culture, and by definite examples relating to caryotypes and exchanges of sister chromatids on cultured adult human keratinocytes.

ORIGIN AND PREPARATION OF THE HUMAN SKIN

Adult human skin is removed during surgical operations.

The thin skin, removed with an electric dermatome, is placed directly into a bottle containing a solution of antibiotics (solution II, see below) and kept at +4° C. for up to 5 days.

The total skin, not cleansed of its fat, is placed in a jar containing solution II. It is kept like this for 24 hours. The fat is then removed from the skin with a surgical knife, and firmly secured, derm downwards, on a cork mat washed with 70° alcohol. The skin is then cut finely by means of an electrokeratome adjusted to a thickness of 0.4 mm. Bearing in mind the variations in the thickness of the epidermis depending on the donor's age and the site from which the skin was removed, this thickness of 0.4 mm corresponds to the total epidermis plus a portion of the papillary layer of the dermis. This thinned-down skin is replaced in solution II and can be kept at +4° C. for up to 3 days.

The thin skin and the total skin so prepared are treated in an identical manner.

The antibiotic rinsing solutions are prepared in 500 ml of Eagle base medium as follows:
SOLUTION I: antibiotic antimycotic product commercially available under the name ABAM (GIBCO):
20 ml
Gentalline: 160 mg
SOLUTION II:
ABAM: 10 ml
Gentalline: 80 mg
SOLUTION III:
ABAM: 5 ml
All the cultures were carried out in the following medium: Dulbecco's Modification of Minimum Eagle Medium (Flow) in Hepes buffer, with the addition of 20% foetal calf serum. 1% of ABAM (Gibco) was added to the total medium.

PREPARATION OF KERATINOCYTE SUSPENSIONS FROM TOTAL THINNED SKIN

The skin is passed successively through the three antibiotic solutions.
SOLUTION I: 30 minutes
SOLUTION II: 30 minutes
SOLUTION III: 3 times 10 minutes.
Between each bath it is blotted on a sterile gauze pad. The skin is then stored in solution III.

For cutting up, the skin is spread, derm down, on the cap of a sterile glass Petri dish. It is cut into fragments measuring some 0.25 cm with a sterile surgical knife.

The fragments are then placed in a 0.25% trypsin solution (Flow) in a Dulbecco phosphate buffer free of calcium and magnesium (PBS-Flow), in amounts of about twenty fragments for 5 ml of trypsin solution in 50 ml conical tubes (Falcon 2070). The tubes are put in a refrigerator at +4° C. for one night. The next morning the fragments are picked out with a big sterile forceps and placed on the cap of a sterile glass Petri dish. They are spread out with the epidermis against the glass. The derm and epiderm are easily separated with two fine forceps. All the fragments are separated in this way and placed in a tube containing 5 ml PBS. The cap is rinsed with 2 ml PBS which is added to the tube. Once the tubes are ready, they are vigorously agitated at 80 r.p.m. (Vortex), which makes it possible to detach the cells from the surface of the derm and to dissociate the lower layers of the epidermis. The PBS containing the derm-+epiderm+dissociated cells is poured into a beaker through two layers of sterile gauze, making it possible to retain the derm, the epiderm and the big cellular aggregates.

The suspensions so recovered are returned to the tubes and centrifuged at 800 r.p.m. for 10 minutes. The PBS is thrown away and the cellular bottoms are put into suspension again in 4 ml of complete medium per tube.

Cells are counted after dilution to ½ of an aliquot in Trypan Blue with a Burker hematimeter.

STUDY OF THE STIMULATION OF ADULT HUMAN KERATINOCYTES BY RE (a) Trials with 100,000 cells per $cm^2$.

Cell suspensions are adjusted in a complete medium to 400,000 cells per ml and applied to two Costar type slides with 24 holes in amounts of 0.5 ml of the suspension per hole.

The plates are placed in a drying oven at 37° C. for 24 hours (day 1); the medium is renewed every second day and, on one of the plates, 10 $\mu l$ of RE, corresponding to 100 $\mu g$ of protein, are added to all the holes every day. The other plate is used as a control. On the 8th day the culture medium is thrown away from both plates, the cells are rinsed in PBS and fixed by Carnoy fixative (methyl alcohol: 3 volumes, acetic acid: 1 volume) for 20 minutes at ambient temperature, then dried in the drying oven at 37° C. for one hour. The cultures are then stained (Giemsa RAL: 4 volumes; Sorenson phosphate buffer pH 6.7:4 volumes; deionized water: 92 volumes) for 10 minutes, rinsed with deionized water and left on filter paper until completely dry.

(b) Trials using a variable number of cells

The cell suspensions are adjusted in a complete medium to $10^5$, $2.10^5$, $4.10^5$, $8.10^5$, $12.10^5$, $16.10^5$ cells per ml. Each dilution is divided between four holes in two plates in ascending order, at a rate of 0.5 ml per hole.

Two plates are thus filled and put into an oven at 37° C. The plates are then treated exactly as in the preceeding trials (a), one of them being subjected to the action of RE, the other acting as control. Fixing and staining are carried out on the 8th day in exactly the same way.

The stained surface visible in the holes and the intensity of staining indicate the intensity of cell growth. In order to quantify this growth and to check that it is not a question of cells being better spread out, mitoses were counted.

In each hole of each plate, the number of mitoses present in five microscropic fields at a magnification of ×250 were counted. The number of mitoses per field were counted for each starting cell dilution, and the results between the RE-treated cultures and the control ones were compared.

The purity of the cultures was tested by submitting them to reaction with leucine aminopeptidase (LAP) (See article by NACHLAS et al., op. cit.). This reaction was found to be negative, while it was positive for nonepidermal cells.

PREPARATION OF CHROMOSOME SPREADS

Cultures for cytogenetic trials were placed on glass slides in Leighton tubes.

The Keratinocytes were adjusted to a concentration of 400,000 cells per ml in a complete medium and divided up in amounts of 2 ml per tube in Leighton tubes with a glass slide on the flattened portion. The tubes were then sealed and placed horizontally in an oven at 37° C.

The medium was changed after 48 hours and after 5 days culturing.

On the 8th day of incubation, 40 µl (400 µg of protein) of RE are added to the tubes. On the 9th day, the medium is thrown away and replaced by fresh medium; 40 µl of RE are added again. Eight days after the last addition of RE, the cultures are treated with a dicolcine salt, commercially available under the trade name "Colcemid" (Gibco), at a final concentration of $0.25.10^6$M for 15 hours.

Mitoses stimulated by RE and blocked during metaphases by the action of "Colcemid" are prepared on slides.

After 15 hours contact with "Colcemid" the slides are washed with PBS, removed from the tubes and placed in 6 cm diameter Petri dishes (Falcon 1007), so that the development of cells during the treatment can be followed with a reversed phase contrast microscope.

The slides are covered with 2 ml hypotonic medium of the following composition:
KCl 0.075M: 25 vol.
distilled $H_2O$: 25 vol.
Injectable hyaluronidase (Choay): 3 vol.

This solution is preheated for 30 minutes at 37° C. The dishes containing the slides are placed in the oven at 37° C. for 30 minutes. The hyaluronidase enables the aqueous medium to penetrate the cells undergoing mitosis and causes them to swell. The dishes are then removed from the oven and the following fixative is added:
absolute methyl alcohol: 3 volumes
glacial acetic acid: 1 volume.

This solution is added drop by drop, very slowly to obtain a dilution of 1:1 in the hypotonic medium in about one hour.

The dishes are then returned to the oven at 37° C. for 10 minutes. The hypotonic medium-fixative mixture is then removed from the dishes and replaced by pure fixative for 20 minutes.

This very slow fixing enables the alcoholic solution to gradually replace the water in the swollen cells.

The slides are removed from the dishes, placed on a metal carrying means, dried in the oven at 37° C. for one hour and stained with Giemsa for ten minutes.
Giemsa (RAL): 4 volumes
Sorensen phosphate buffer, pH 6.7: 4 volumes
distilled $H_2O$: 92 volumes To obtain R bands on the preparations, the heat denaturation technique was used (DUTRILLAUX et al. 1972, CHARPENTIER et al. 1972). For this, the unstained slides are placed in a tube containing an Earle salt solution, pH 6.5 at 87° C. The tubes are maintained in a water bath at this temperature for a time varying in a manner inversely proportional to the age of the preparations. For 15 days old preparations this time is approximately thirty minutes.

The slides are then removed from the tubes, rinsed with distilled water and stained with the Giemsa stain previously used.

After 10 minutes staining, the slides are rinsed in demineralized water, blotted between two filter papers and left to dry in the air for two hours.

The slides are fixed with DPX (GURR) onto histology slides.

PREPARATION OF CHROMATID EXCHANGES

Preparation and the starting of cultures are identical to those described for chromosomic preparations. On the 8th day, the culture medium is thrown away and replaced by fresh medium containing bromodeoxyuridin (BUdR Sigma) at a final concentration of 0.5 µg per ml. 40 µl (400 µg) of protein) of RE are added to each tube and these are replaced in the oven at 37° C. On the 9th day the medium is thrown away and replaced by medium also containing BUdR at the same concentration. The same amount of RE is added. Eighteen hours later, the cultures are treated with Colcemid (Gibco): $0.25\ 10^6$M as before, for 15 hours.

The preparation of metaphases is identical to that described above.

The BUdR is incorporated during two consecutive cycles in the place of thymidin in the ADN of a majority of cells, stimulated by the RE. The metaphasic chromosomes, after the second replication cycle, have one chromatid bisubstituted by BUdR and one monosubstituted chromatid. The latter fixes the Hoechst 33258 fluorochrome, which is then replaced by Giemsa. The technique used is derived from the DE WEERDKASTELEIN et al. (1977) technique, itself adapted from the method described by PERRY et al. (1974). The slides are plunged into a Hoechst 33258 (Hoechst) fluorochrome solution at 0.5 µg per ml of PBS for 15 minutes. They are then placed, cells down, in 6 cm diameter Petri dishes containing a filter paper moistened with PBS under an UV lamp (254 nm) for one night.

The cells are then placed in a water bath at 61° C. for one hour, in tubes containing a buffer:
KCl: 0.3M
Sodium citrate: 0.03M The slides are then rinsed in distilled water, stained with Giemsa, dried and mounted as above.

Chromosome observation and counting and chromatid exchanges were effected with an orthoplaned microscope with an immersion objective.

EXAMPLE I

Increase in cellular density and the area covered with adult human epidermal keratinocytes after treatment with retinian extract (RE)

In this representative experiment, a 2 to 3 cm² specimen of skin was removed from the thoracic area of a 30 years old woman. This specimen was cut into thinned 2 to 4 mm² fragments. These fragments were incubated one night in 0.25% trypsin in a phosphate buffer salt (PBS) at +4° C. Once they had dissociated, the epidermis and the derm were gently agitated in PBS to obtain the cells. After filtration through two-ply gauze, the cells were sedimented at 800 r.p.m. for 10 minutes. The culture medium (T.C.M.) consisted of the modification of Dulbecco of Eagle MEM in a Hepes buffer with 20% foetal calf serum added. Tissue culture plates (COSTAR-3524) with 24 holes (2 cm² per hole), were seeded with various cell concentrations.

Bovine retinas were used to prepare RE as follows:

Ox eyes are removed at the slaughter house a few moments after the animals are dead. They are transported on ice and dissection is carried out within the following 3 hours. After the eyeball has been cleaned by a jet of alcohol at 70%, the cornea is cut and the crystalline lens, the iris and the vitreous humour are placed in separate containers on ice. The retina is then removed with forceps and washed in a neutral isotonic buffer solution. The retinas are then collected together.

All the consecutive steps of extracting the RE are carried out under cold.

50 retinas are put into 50 ml of PBS buffer and then ground in a Potter. A first centrifugation is effected at 11,000 r.p.m. for 30 minutes. The supernatent is then directly filtered through a succession of "Millipore" filters with decreasing pore diameter: $3\mu$, $1.2\mu$, $0.45\mu$, $0.22\mu$, the last providing sterilization. The RE is conserved frozen.

RE can also be obtained, with similar yields, by performing:

(1°) An additional centrifugation at 100,000 g before the filtrations, (2°) a dialysis against the PBS buffer for one night, followed by the sterilization filtration.

The protein solution was adjusted to 5 mg per ml with respect to PBS. The protein content was measured by the technique described by BRADFORD M. M., Analytical Biochem. 72, 248–254 (1976) using bovine albumin serum (fraction V) as a standard, 20 μl per hole (0.5 ml of TCM) were added each day, as follows: At 24 h the RE was added, the TCM was removed on the 2nd day and replaced by TCM+RE. On day 3, the RE was added without changing the RE. On day 4, the TCM was removed and replaced by fresh TCM+RE. On days 5 and 7, the cultures were treated as on day 3, on days 6 and 8, as on day 4. The controls were treated in a similar way but without the R.E.

From left to right the cells were seeded at rates of:
(a) $5 \times 10^4$
(b) $10^5$
(c) $2 \times 10^5$
(d) $4 \times 10^5$
(e) $6 \times 10^5$
(f) $8 \times 10^5$ cells per hole. The effect of RE on the surface covered by epidermal cells is clearly visible in rows (a), (b) and (c). The increase in cellular density can be seen also in rows (c), (d), (e) and (f).

EXAMPLE 2

Increase in mitotic activity as a result of treatment with RE

The mitotic figures were counted in the cultures. For this, 5 microscopic fields were examined under a magnification of ×250, in each hole. The number of mitotic figures per microscopic field (ordinates) was marked as a function of the concentration of seeded cells per hole (abscissa). Each point on the curve represented the mean value of 12 counts (3 microscopic fields × 4 holes). In the control cultures, about 3 mitotic figures could be detected in one microscopic field for a seeding concentration of 4, 6.4 and $8 \times 10^5$.

In the cultures treated with RE the number of mitotic figures is at least doubled.

EXAMPLE 3

Accumulation of mitoses for chromosomic charts.

For the chromosomic charts, specimens of skin were taken from 6 adult subjects. The cell suspensions were prepared as was described in example I and adjusted to $2 \times 10^5$ cells per ml in TCM. 2 ml of these suspensions were seeded on $11 \times 22$ m (about 2 cm$^2$) glass slides in Leighton tubes. The 8th and 9th days, 100 μg (protein equivalent) per ml of RE were added to each tube. 12 hours after the 2nd addition of RE, the cells were treated with Colcemid ($0.25 \times 10^6$M) for 15 hours to accumulate the metaphases. The slides were rinsed with PBS and transferred into dishes half filled with hypotonic solution (KCl $0.075M:H_2O:1:1$) to which was added 6% hyaluronidase (Choay). After 30 minutes at $+37°$ C., the fixative (methanol, acetic acid 3:1) was added to the hypotonic solution very slowly, drop by drop, to obtain a 1:1 dilution in about 1 hour. This mixture was replaced after 10 minutes at $+37°$ C. by pure fixative for 30 minutes at ambient temperature.

EXAMPLE 4

Exchanges of sister chromatids on adult human keratinocytes

Adult human keratinocyte cultures (4 trials) were started at a concentration of $4 \times 10^5$ cells per glass slide in a Leighton tube, as in example 3. The cells were cultured for 8 days in normal TCM, without RE, as in example I. On the 8th day, the TCM was removed and replaced by TCM containing BUdR (final concentration 0.2 μg per ml). 100 μg (protein equivalent) of RE was added. After 24 hours at $+37°$ C., the medium was removed and replaced by fresh TCM containing the same amount of BUdR and RE respectively.

The cells were incubated under these conditions for 36 hours. After treatment with Colcemid, the hypotonic solution and the fixative, as is shown in FIG. 3, the cultures were stained with Hoechst 33,358 (0.5 μg per ml in PBS) for 15 minutes. Then, after exposure to U.V. light at 254 nm for one night, the slides were treated with SSC×2 (0.3M KCl, 0.03M sodium citrate) at $+61°$ C. for one hour (DE WEERD-KASTELEIN E. A., KEIZER W., RAINALDI G. and BOOTSMA D. Mutat. Res. 45 253–261 (1977).

The cells were rinsed with water and stained with 4% Giemsa in phosphate buffer pH 6.7 for 10 minutes.

EXAMPLE 5

Comparison of the activity of RE and that of another growth factor (FGF)

The following example is given to demonstrate the difference in the activity of RE and of the factor FGF on myoblast growth (see D. Gospodarowicz's article mentioned hereinabove).

Myoblasts prepared by the dissociation of calf member muscles are seeded in Petri dishes. The culture medium only contains 0.5% serum. For 2 days, the cells receive 50 μl of RE or 10 ng of F.G.F. The number of cells is determined directly on half of the dishes; on the other half, incorporation of radioactive thymidine is measured after 4 hours incubation. The results show that the control contains 40,000 cells and 8100 Cpm, whereas the sample treated with RE contains 120,000 cells and 41,000 Cpm and the sample treated with FGF contains 40,000 cells and 25,000 Cpm.

Therefore, there is marked stimulation due to RE. In this case, the FGF does not modify the number of cells, as compared with the control.

EXAMPLE 6

This example relates to the action of the RE factor on the growth of cultured guinea pig epidermal cells.

The cells were obtained from the ear of an adult Hartley guinea pig (class IV). Three types of cells were isolated:

(a) basal epidermal cells,
(b) suprabasal epidermal cells,
(c) conjunctive dermic tissue cells, The epidermal cells were seeded at three different concentrations: 500,000/cm$^2$-250,000/cm$^2$ and 100,000/cm$^2$.

The fibroblastic cells were seeded at 50,000/cm$^2$ and at 400,000/cm$^2$.

All the cultures were made in an Eagle BME+10% foetal calf serum medium. The cells were cultured in triplicate in plastic Petri dishes.

The RE was added to the culture medium at a rate of 100 µg protein equivalent per ml. The cells were seeded in a culture medium containing RE. The media were changed on the 1st, 3rd, 5th and 8th days and replaced by fresh media also containing the same rate of RE. The cells were therefore maintained in the presence of RE during the entire experiment.

Tritiated thymidine ($^3$H-methyl-thymidine Amersham a. s.40 Ci/mM) was added to the final concentration of 5 µCi/ml.

After incubation for one hour, the medium was removed, the cells were washed once in PBS, then in 0.3M potash directly in the Petri dish for one hour at 37° C. The viscous solution obtained was precipitated with PCA at 70%. The precipitate was washed three times with 0.4M PCA and hydrolyzed in 0.5M PCA for 15 minutes at 95° C.

A supernatent aliquot was counted for radioactivity and another aliquot was used to measure its DNA content according to the Burton technique.

In order to assess desquamation on days 1,3,5 and 8, the cell culture media were recovered and filtered through 0.45µ weighed Millipore filter. 48 hours later, the air-dried filters were weighed again. The dry weight obtained corresponded to the protein content in mg.

RESULTS

The trials reported above show that the RE has a significant effect on DNA synthesis by basal cells on the 8th day at 2×10$^6$ cells, i.e. at the rate of 250,000 cells/cm$^2$. The effect is less constant on the same cells at 500,000 per cm$^2$.

The induction effect is especially clear on the 8th day on mature (suprabasal) cells seeded at a rate of 250,000/cm$^2$.

Finally, no effect was observed at 8 days on derm cells (mainly fibroblasts).

Furthermore, desquamation is not modified.

On the whole RE was shown to be an activator in epidermal cells (basal+suprabasal) seeded at 250,000 per cm$^2$ after the cells have been exposed to the product for 8 days. Under the same conditions, the action was non-existant for dermic cells.

It is seen, therefore, that RE has a stimulating effect on the in vitro growth of adult epidermal cells both in man and in the guinea pig.

EXAMPLE 7

Additional experiments were conducted to demonstrate the absence of side effects of RE.

Study on the mutagen activity of RE on various strains of *Salmonella typhimurium* and at concentrations of 22.5 to 720 µg/culture, showed no mutagen effect according to the Ames method.

At a concentration of 100 µg/ml, RE caused no local irritation of the skin.

The irritation rating on the ocular conjunctiva, at a concentration of 5 mg/ml, also showed no irritant effect for rabbit eye.

We claim:

1. A process for stimulating the growth of epiderm cells, which comprises contacting the epiderm cells with an aqueous saline extract of ocular tissue (RE).

2. The process according to claim 1, wherein the active agent is extracted from eye tissues inclusive of the choroid, the iris and the vitreous humour.

3. The process according to claim 2, wherein the RE is obtained by the treatment of bovine ocular tissues with a buffered aqueous saline solution with a pH of about 7.2.

4. The process according to claim 3, wherein there is used 50 to 400 µg, in total protein, of extract per ml of epidermal cell culture.

5. The process according to claim 4, wherein the culture is a culture of human epiderm cells.

6. The process according to claim 5 wherein said human epiderm cell is suitable for the detection of natural or induced chromosome anomalies.

7. The process according to claim 6 wherein said human epiderm cell is suitable for the assessment of sister chromatid exchanges (SCE) in in vitro cultures of adult human keratinocytes.

8. The process according to claim 7, which further comprises first effecting a preliminary normal culturing of epidermal cells in the absence of the growth factor RE, and then introducing therein after a period of about 5 to 10 days, an effective amount of RE and, then introducing about one or two days later, another effective amount of RE and obtaining a second replication of the cells.

9. The process according to claim 7, wherein the culturing of epidermal cells is effected by introducing, at the beginning, an effective amount of RE and then arresting the culturing to permit cell synchronization.

10. The process according to claim 5 resulting in grafts.

11. The process according to claim 10 which further comprises integrating said process into a grafting technique comprising removing small fragments of skin for a subsequent autograft, splitting the graft by enzymatic means 1 to 2 weeks before the culture, causing the cultured epidermal cells to proliferate on a substrate comprising thin flaps of human skin or pig skin, the RE being added in an effective amount for quick cultivation of epidermal cells, and effecting the graft in a conventional manner.

12. The process of anyone of claims 1 to 5 comprising the long-term culturing of epidermal cells.

13. The process according to claim 12, wherein the cells are cultured directly on a substrate in the presence of an effective amount of RE and without the addition of other cells.

14. The process of claim 10 wherein said graft is suitable for treatment of burns.

* * * * *